United States Patent [19]

Negishi et al.

[11] Patent Number: 5,696,299

[45] Date of Patent: Dec. 9, 1997

[54] OPTICAL RESOLUTION FOR PRODUCING OPTICALLY ACTIVE ALCOHOL

[75] Inventors: Satoshi Negishi, Tokyo; Seiichi Shirasawa; Junko Suzuki, both of Kanagawa; Yukie Masuda, Tokyo, all of Japan

[73] Assignee: The Nisshin Oil Mills, Ltd., Tokyo, Japan

[21] Appl. No.: 529,059

[22] Filed: Sep. 15, 1995

[30] Foreign Application Priority Data

Oct. 26, 1994 [JP] Japan .................................. 6-284513
Oct. 26, 1994 [JP] Japan .................................. 6-284514
Oct. 26, 1994 [JP] Japan .................................. 6-284515

[51] Int. Cl.$^6$ ........................... C07C 33/18; C07C 33/46
[52] U.S. Cl. .......................... 568/715; 568/812; 568/813; 568/840; 568/841; 568/876; 568/877
[58] Field of Search .......................... 568/715, 812, 568/813, 841, 876, 877, 840

[56] References Cited

U.S. PATENT DOCUMENTS

| | | |
|---|---|---|
| 4,665,029 | 5/1987 | Iwai et al. . |
| 4,882,451 | 11/1989 | Yoshida et al. . |
| 4,962,031 | 10/1990 | Yoshida et al. . |
| 5,256,569 | 10/1993 | Yoshida et al. . |

FOREIGN PATENT DOCUMENTS

| | | |
|---|---|---|
| 58-36953 | 8/1983 | Japan . |
| 59-156282 | 9/1984 | Japan . |
| 60-15312 | 4/1985 | Japan . |
| 62-166898 | 7/1987 | Japan . |
| 63-273499 | 11/1988 | Japan . |
| 63-284184 | 11/1988 | Japan . |
| 2-86797 | 3/1990 | Japan . |
| 2-282340 | 11/1990 | Japan . |
| 4-349894 | 12/1992 | Japan . |

*Primary Examiner*—Paul F. Shaver
*Attorney, Agent, or Firm*—Nikaido, Marmelstein, Murray & Oram LLP

[57] ABSTRACT

A process for producing an optically active alcohol comprising carrying out interesterification between a racemic alcohol and an ester selected from the group consisting of (a) a diester between a lower monohydric alcohol and a saturated dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms in the presence of lipase, preferably heat-resistant lipase, and in the presence or absence of a solvent, preferably in the absence of a solvent, under a substantially water-free condition, separating an optically active alcohol rich in either one of R- and S-forms from the reaction mixture, and adding an optically inactive non-racemic alcohol to the residue of the previous step to carry out interesterification under the same conditions as in the previous reaction to separate the other enantiomer. According to the present invention a racemic alcohol can easily be resolved into each enantiomer with high purity in good yield.

10 Claims, No Drawings

OPTICAL RESOLUTION FOR PRODUCING OPTICALLY ACTIVE ALCOHOL

FIELD OF THE INVENTION

This invention relates to an optical resolution process for producing an optically active alcohol which is important as an intermediate for synthesis of fine chemicals, such as starting materials or intermediate materials for pharmaceuticals or agricultural chemicals and liquid crystals.

BACKGROUND OF THE INVENTION

Optically active alcohols are important substances as intermediates of syntheses in the fine chemical field, such as starting materials or intermediate materials for pharmaceuticals or agricultural chemicals and liquid crystalline materials. They are required to have considerably high chemical purity and optical purity in order to exhibit sufficient physiological activities or characteristics. On the other hand, reactions using an enzyme, such as lipase, lipoprotein lipase or esterase, enable discrimination of enantiomers, which is difficult in ordinary chemical reactions accompanied by high temperatures. These enzymatic reactions are effective means for increasing the optical purity, i.e., means for carrying out optical resolution, and production of optically active alcohols making use of the enzymatic reactions has recently been studied.

However, enzyme reactions heretofore proposed take a very long time of from several days to several tens of days (see JP-A-62-166898, JP-A-63-273499 and JP-A-2-86797, the term "JP-A" as used herein means an "unexamined published Japanese patent application"). Moreover, the temperature range in which an enzymatic reaction is possible is from about 20° to 70° C., preferably from 30° to 50° C., at the broadest in the case of lipase. An ester, for example, which is to be interesterified with a racemic alcohol must be liquid in that temperature range or otherwise must be dissolved in a solvent as described in JP-A-62-166898, JP-A-63-284184, JP-A-2-282340, and JP-A-4-349894.

Generally, the ester and the racemic alcohol which are subjected to interesterification have similar physical properties, such as a boiling point or a melting point. Since the reaction mixture usually comprises various components such as unreacted substances and by-products as well as a desired product, general purification means taking advantage of a difference in physical properties are hardly applicable for efficiently isolating a desired product from the reaction mixture and increasing chemical and optical purity, and other complicated and expensive steps should be used in purification. That is, under the present situation, the reaction mixture after completion of interesterification must be subjected to a further treatment such as hydrolysis in order to recover a desired optically active alcohol, and the product should be purified by azeotropic distillation, molecular distillation or preparative liquid chromatography to increase the chemical purity.

As mentioned above, the processes so far proposed for producing optically active alcohols using an enzyme has a disadvantage that they require a very long reaction time. Further, since the enzymatic reaction temperature is practically limited to a narrow range of from 30° to 50° C. and starting materials should be chosen according to temperature suitability, differences in physical properties, such as a melting point or a boiling point, are hardly utilized for the isolation and purification after the reaction. Thus, there was a problem that complicated processes are necessary and a great cost is entertained for efficient recovery of a desired optically active alcohol from the reaction mixture.

SUMMARY OF THE INVENTION

An object of the present invention is to provide a process for producing an optically active alcohol by optical resolution, in which an enzymatic reaction can be achieved in a reduced time and a desired product can be separated and purified through simple and easy operation.

The inventors of the present invention have conducted extensive study for the purpose of overcoming the aforementioned problems and of providing an optically active alcohol by an industrially simple, easy, and advantageous method. As a result, they have found that interesterification between a racemic alcohol and a specific ester hereinafter described in the presence of lipase and in the presence or absence of a solvent gives a reaction mixture from which one of enantiomers, i.e., an optically active alcohol can easily be isolated in high yield (hereinafter called a first reaction). They have further found that the other enantiomer can then be isolated in high yield with ease by adding an optically inactive non-racemic alcohol to the residue of the first reaction after isolation of the optically active alcohol and carrying out interesterification in the presence of lipase in the same manner as in the first reaction (hereinafter called a second reaction). They have furthermore found that the first reaction completes in an extremely short time when the reaction is carried out in the presence of heat-resistant lipase at an elevated reaction temperature; that one of the enantiomers can easily be isolated from the resulting reaction mixture in high yield; and that the other enantiomer can easily be isolated in high yield from the residue of the first reaction after isolation of the optically active alcohol by adding a specific optically inactive non-racemic alcohol to the residue followed by interesterification in the presence of heat-resistant lipase in a high temperature and under reduced pressure. The present invention was achieved based on these finds.

Thus, the present invention provides:

1. a process for producing an optically active alcohol comprising the steps of:
   carrying out interesterification between a racemic alcohol and an ester selected from the group consisting of (a) a diester between a lower monohydric alcohol and a saturated dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms in the presence of heat-resistant lipase and in the absence of a solvent under a substantially water-free condition at a temperature of not lower than 81° C. and
   separating an optically active alcohol rich in either one of R- and S-forms from the reaction mixture;
2. a process for producing an optically active alcohol comprising the steps of:
   carrying out interesterification between a racemic alcohol and an ester selected from the group consisting of (a) a diester between a lower monohydric alcohol and a saturate dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms in the presence of lipase and in the presence or absence of a solvent under a substantially water-free condition,
   separating the resulting reaction mixture into an optically active alcohol rich in either one of R- and S-forms and the residue, adding an optically inactive non-racemic alcohol having a different boiling point from that of the racemic alcohol to the residue to carry out interesterification in the presence of lipase and in the presence or absence of a solvent under a substantially water-free condition, and separating an optically active alcohol rich in either one of R- and S-forms which has not been separated in the second step;

3. a process for producing an optically active alcohol comprising the steps of:

carrying out interesterification between a racemic alcohol and a diester between a lower monohydric alcohol and a saturated dicarboxylic acid having 14 or more carbon atoms in the presence of heat-resistant lipase and in the absence of a solvent under a substantially water-free condition at a temperature not lower than 81° C., separating the resulting reaction mixture into an optically active alcohol rich in either one of R- and S-forms and the residue, and adding an optically inactive non-racemic saturated alcohol having 16 or more carbon atoms to the residue to

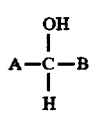
(I)

wherein A and B are different from each other; A represents a phenyl group or a substituent represented by formula (II):

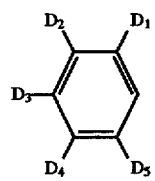
(II)

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms;

and B represents an alkyl group having 1 to 3 carbon atoms, a trifluoromethyl group or a cyano group;

8. the process for producing an optically active alcohol of above 2, wherein the lipase is a heat-resistant lipase and the interesterification is carried out at a temperature of not lower than 81° C.

9. the above-mentioned process for producing an optically active alcohol, wherein the heat-resistant lipase is a heat-resistant lipase produced by a microorganism belonging to the genus Alcaligenes; and 10. the above-mentioned process for producing an optically active alcohol, wherein the interesterification using heat-resistant lipase is carried out at the temperature of from 101° to 120° C.

DETAILED DESCRIPTION OF THE INVENTION

While the racemic alcohol which can be used in the present invention is not particularly limited, 2-alkanols are preferred because of the easy optical resolution. Further, racemic alcohols represented by formula (I):

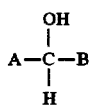
(I)

wherein A and B are different from each other; A represents a phenyl group or a substituent represented by formula (II):

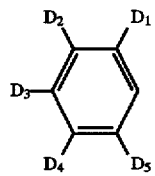
(II)

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms; carry out interesterification in the presence of heat-resistant lipase and in the absence of a solvent under a substantially water-free condition at a temperature of not lower than 81° C. and under reduced pressure while separating an optically active alcohol rich in either one of R- and S-forms which has not been separated in the second step by reduced pressure distillation.

4. the above-mentioned process for producing an optically active alcohol, wherein the saturated dicarboxylic acid and the saturated fatty acid have a straight chain structure;

5. the above-mentioned process for producing an optically active alcohol, wherein the lipase or heat-resistant lipase has a powdered form and at least 90% (as an absolute number) of the lipase has a particle size of from 1 to 100 μm;

6. the above-mentioned process for producing an optically active alcohol, wherein the racemic alcohol is a 2-alkanol;

7. the above-mentioned process for producing an optically active alcohol, wherein the racemic alcohol is a compound represented by formula (I):

and B represents an alkyl group having 1 to 3 carbon atoms, a trifluoromethyl group or a cyano group, are also preferred for efficient optical resolution by the process of the present invention.

Specific examples of these racemic alcohols are 2-butanol, 2-pentanol, 2-hexanol, 2-heptanol, 2-octanol, 2-nonanol, 2-decanol, 1-phenylethanol, 1-phenyl-1-propanol, ethyl 3-hydroxybutanate, ethyl 3-hydroxypropionate, methyl 3-hydroxypentanate, 1-phenyl-1,3-propanediol, 2-phenyl-1-cyclohexanol, 1-pentyn-3-ol, 1-(2-bromophenyl)ethanol, 1-p-chlorophenylethanol, 1-(4-chlorophenyl)ethanol, 1-chloro-2-octanol, 1,1-difluoro-2-octanol, and 1-(2,4-dichlorophenyl)ethanol. Among these racemic alcohols, 2-octanol, 1-phenylethanol, 1-phenyl-1,3-propanediol, and 2-phenyl-1-cyclohexanol are preferable. 1-Phenylethanol, 2-octanol, and 1-(2-bromophenyl)ethanol are the most preferable.

The ester which can be used in the first step of the process of the present invention is at least one ester selected from the group consisting of (a) a diester between a lower monohydric alcohol and a saturated dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms. The term "lower monohydric alcohol" as used herein means a straight-chain or branched monohydric alcohol having 1 to 3 carbon atoms, such as methanol, ethanol, n-propanol, and isopropyl alcohol. It is desirable that all the esters (a), (b) and (c) have a high melting point, preferably not lower than 60° C., still preferably not lower than 70° C., so that a desired optically active alcohol may be recovered efficiently from the interesterification reaction mixture.

Diesters (a) between a dicarboxylic acid and a lower alcohol include dimethyl, diethyl, di-n-propyl or diisopropyl esters of a saturated dicarboxylic acid, such as tetradecadicarboxylic acid, pentadecadicarboxylic acid, hexadecadicarboxylic acid, heptadecadicarboxylic acid, octadecadicarboxylic acid, nonadecadicarboxylic acid, eicosadicarboxylic acid, docosadicarboxylic acid, tetracosadicarboxylic acid, hexacosadicarboxylic acid, octacosadicarboxylic acid, and a dimer acid derived from oleic acid, erucic acid, etc. Among these diesters, lower monohydric alcohol diesters of straight-chain, saturated dicarboxylic acids having 20 to 28 carbon atoms are preferable, and lower monohydric alcohol diesters of a dicarboxylic acid having 22 carbon atoms (i.e., docosadicarboxylic acid) or a dicarboxylic acid having 28 carbon atoms (i.e., octacosadicarboxylic acid) are more preferable. If the dicarboxylic acid has less than 14 carbon atoms, a desired product cannot be separated efficiently in the purification step. Dicarboxylic acids having more than 45 carbon atoms are not easily available on an industrial scale. Monohydric alcohols having more than 3 carbon atoms are not favorable because of a possibility of containing a racemic modification.

Fatty acid triglycerides (b) include tripalmitin (triglyceride of palmitic acid ($C_{16}$)), tri-2-hexyldecan (triglyceride of 2-hexyldecanoic acid ($C_{16}$)), tristearin (triglyceride of stearic acid ($C_{18}$)), triisostearin (triglyceride of 2-heptylundecanoic acid or isostearic acid produced by Emery Co., Ltd. ($C_{18}$)), triarachidin (triglyceride of arachidic acid ($C_{20}$)), tribehen (triglyceride of behenic acid ($C_{22}$)), trilignocerin (triglyceride of lignoceric acid ($C_{24}$)), tricerotin (triglyceride of cerotic acid ($C_{26}$)), trimontan (triglyceride of montanic acid ($C_{28}$)), trimelissin (triglyceride of melissic acid ($C_{30}$)), trilaccerin (triglyceride of lacceric acid ($C_{32}$)), and trigeddin (triglyceride of geddic acid ($C_{34}$)).

The three fatty acid moieties in the triglyceride may be either the same (simple triglyceride) or different at an arbitrary ratio (mixed triglyceride). A mixture of simple triglycerides at an arbitrary ratio may also be used. In addition, hydrogenation products of fish oils, animal fats and oils, and vegetable fats and oils (i.e., hardened fats and oils) mainly comprise the above-mentioned fatty acids as the constituent fatty acid components thereof and are therefore useful as they are in the present invention. Examples of useful hydrogenated fats and oils include hydrogenation products of sardine oil, herring oil, saury oil, cuttlefish oil, cod liver oil, menhaden oil, seal oil, beef tallow, lard, mutton tallow, linseed oil, perilla oil, walnut oil, sunflower oil, safflower oil, soybean oil, cotton seed oil, corn oil, sesame oil, rape seed oil, rice bran oil, peanut oil, olive oil, camellia oil, tea seed oil, castor oil, palm oil, etc. In the present invention, triglycerides of the above-mentioned straight-chain saturated fatty acids are preferably used.

Of these fatty acid triglycerides, those having fatty acid moieties containing 16 to 30 carbon atoms and hydrogenated fish oils or animal or vegetable fats and oils are preferred, with tristearin, tribehen, extremely hardened soybean fat and oil, and extremely hardened rape seed fat and oil being still preferred. Tribehen and extremely hardened rape seed fat and oil are especially preferred. Those having fatty acid moieties containing less than 16 carbon atoms are unfavorable because a desired product cannot be separated efficiently in the purification step, and those having fatty acid moieties containing more than 34 carbon atoms are not easily available on an industrial scale.

Examples of useful monoesters (c) between a fatty acid and a lower alcohol include methyl, ethyl, n-propyl and isopropyl esters of stearic acid, isostearic acid (e.g., 2-heptylundecanoic acid and isostearic acid produced by Emery Co., Ltd.), arachidic acid, behenic acid, lignoceric acid, cerotic acid, montanic acid, melissic acid, lacceric acid, geddic acid, etc. or a mixed fatty acid comprising these fatty acids at an arbitrary ratio (e.g., a mixed fatty acid obtained by hydrolysis of a hydrogenation product of the above-described fish oils, animal fats and oils, and vegetable fats and oils or a hydrogenation product of a mixed fatty acid obtained by hydrolysis of the above-described fats and oils). Among these monoesters, preferred ones are lower monohydric alcohol monoesters of the above-mentioned straight-chain saturated fatty acids having 18 to 30, more preferably 20 to 28, and most preferably 22 to 28, carbon atoms. If the fatty acid moiety in the monoester has less than 18 carbon atoms, a desired product is difficult to separate in the purification step. Fatty acids containing more than 34 carbon atoms are not easily available on an industrial scale.

The order of preference in making a choice of the ester to be used is diester (a), monoester (c), and triglyceride (b). Diester (a) is particularly recommended since the scale of the reaction system can be reduced. That is, the amount of starting materials used and the amount of lipase used can be reduced and, therefore, a smaller apparatus can be used for the reaction.

Other esters that may be used include various waxes, which are esters of higher fatty acids and higher alcohols, such as montan wax, carnauba wax, rice wax, candelilla wax, sunflower wax, bees wax, whale wax, shellac wax, insect wax, poppy seed wax, cotton wax, and sugar cane wax.

In the first step of the present invention, the above-described raw materials are subjected to interesterification using lipase as a catalyst. Known lipase species can be utilized, including swine pancreatic lipase (e.g., Pancreatin F produced by Amano Pharmaceutical Co., Ltd. and Swine Pancreatic Lipase Grade Type II produced by Sigma Chemical Company) and lipase of microorganism origin, for example, lipase of *Pseudomonas fluorescens* (e.g., Lipase P produced by Amano Pharmaceutical Co., Ltd.), lipase from *Pseudomonas sp.* (e.g., Lipase PS and Lipase AK produced by Amano Pharmaceutical Co., Ltd. and Lipase P produced by Nagase & Co., Ltd.) lipase of *Candida cylindoracea* (e.g., Lipase OF produced by Amano Pharmaceutical Co., Ltd.), lipase of *Aspergillus niger* (e.g., Lipase A produced by Amano Pharmaceutical Co., Ltd.), lipase of *Mucor miehei* (e.g., Lipozyme produced by Novo Nordisk Bioindustry), lipase of *Mucor javanicus* (e.g., Lipase M produced by Amano Pharmaceutical Co., Ltd.), lipase of *Rhizopus delemar* (e.g., Lipase D produced by Amano Pharmaceutical Co., Ltd.), lipase of *Rhizopus niveus* (e.g., Lipase N produced by Amano Pharmaceutical Co., Ltd.), lipase of *Rhizopus javanicus* (e.g., Lipase F-AP produced by Amano Pharmaceutical Co., Ltd.), lipase of *Humicola lanuginosa* (e.g., Lipase CE produced by Amano Pharmaceutical Co., Ltd.), lipase of *Chromobacterium viscosum* (e.g., Lipase produced by Toyo Jyozo Co., Ltd., now Asahi Kasei Kogyo Kabushiki Kaisha), lipase of *Geotrichum candidum* (e.g., Lipase GC produced by Amano Pharmaceutical Co., Ltd.), lipase of *Penicillium cyclopium*, etc. These lipase species can be used either as powdered or as immobilized on a known carrier, such as activated carbon, Celite, adsorbing resins, ion-exchange resins, glass, or ceramics (cf. *Ripaze sonokiso to oyo* (Lipase, Fundamentals and Application), pp. 336–343, 1991, published by Saiwai Syobo).

The above-described alcohol and ester are used at an alcohol:ester molar ratio of 1:≦1, preferably 1:1 to 1:0.5, as a starting material of interesterification. The interesterification reaction can be carried out by dispersing lipase, preferably powdered lipase, in a substantially water-free reaction system comprising the starting material with or without a solvent for the starting material, such as nonaqueous organic solvents (e.g., hexane, cyclohexane, heptane, octane, iso-octane, carbon tetrachloride, diethyl ether, diisopropyl ether and petroleum ether) while stirring. The term "substantially water-free" as used herein means that the water content of the reaction system should be not more than about 0.1% by weight, which is an equivalent water content of the starting material, preferably not more than 0.01% by weight. It is desirable to carry out interesterification with the particle size of the lipase powder being controlled in such a manner that not less than 90% (as an absolute number) of the lipase particles have a particle size in the range of from 1 to 100 μm, preferably from 20 to 50 μm. Such a particle size distribution can be obtained by dispersing lipase powder in the starting material (melted by heating if desired) and subjecting the dispersion to ultrasonication, filtration using a precision membrane or an ultrafiltration membrane, centrifugal sedimentation, and the like. Preferably, ultrasonication under conditions of a temperature lower than the reaction temperature, 20 to 150 kHz, and 100 to 250 W for 1 to 30 minutes would be convenient.

The reaction temperature is selected from the range of from 20° to 130° C. taking into consideration heat resistance of lipase and the boiling point of a solvent. The reaction is performed with mild stirring or shaking for a prescribed period of time, preferably several to 100 hours while monitoring the reaction rate through, for example, gas chromatography. If the reaction temperature is lower than 20° C., the reaction progress is slow. If it exceeds 130° C., lipase will be inactivated.

It is preferable to use heat-resistant lipase in the interesterification reaction of the present invention, whereby the interesterification reaction between the racemic alcohol and the above-described ester can be kept at a high temperature to facilitate smooth progress. In addition, a high temperature reaction permits use of a high-melting ester without requiring a solvent for dissolving the starting material as has conventionally been needed.

Examples of the heat-resistant lipase species preferably include the one of genus Alcaligenes origin described in JP-B-58-36952 (the term "JP-B" as used herein means an "examined published Japanese patent publication") and the one of *Rhizopus chinensis* origin described in JP-A-59-156282. In particular, lipase PL-266 produced by *Alcaligenes sp.* PL-266 (FERM P-3187) disclosed in JP-B-58-36953, which is available as Lipase QL produced by Meito Sangyo Co., Ltd., and lipase PL-679 produced by *Alcaligenes sp.* PL-679 (FERM P-3783), which is available as Lipase PL produced by Meito Sangyo Co., Ltd., are preferred in the present invention. Lipase QL is more preferable. Heat-resistant lipase may be used as immobilized on a known carrier, such as activated carbon, Celite, adsorbing resins, ion-exchange resins, glass, or ceramics, but is preferably added to the starting material in the form of powder as hereinafter described.

The interesterification reaction utilizing the heat-resistant lipase may be carried out under the same conditions described above, and it is advantageous to carry out the reaction without using a solvent.

In using heat-resistant lipase, e.g., the above-described Lipase PL-266 (product name: Lipase QL produced by Meito Sangyo Co., Ltd.) and Lipase PL-679 (product name: Lipase PL produced by Meito Sangyo Co., Ltd.), the reaction temperature is set preferably at 81° C. or higher, more preferably from 91° to 130° C., most preferably from 101° to 120° C., and the reaction is performed with mild stirring or shaking for a prescribed period of time, preferably 10 minutes to 10 hours wile monitoring the reaction rate through, for example, gas chromatography. If the reaction temperature is lower than 81° C., the reaction progress is slow. Temperatures exceeding 130° C. incurs inactivation of lipase. In the first reaction, some of the starting esters produce a lower alcohol by the interesterification reaction. In such as case, the reaction may be carried out while evaporating the produced lower alcohol under reduced pressure thereby increasing efficiency of the reaction.

The resulting reaction mixture contains an optically active alcohol rich in either one of R-form and S-form as an unreacted substance. In the second step, this optically active alcohol is isolated from the reaction mixture with a high purity by first removing lipase using a precision filtration membrane such as filter paper and then purifying by a relatively simple means, such as simple distillation, fractionation with or without a solvent, recrystallization, silica gel column chromatography, and so on, preferably simply by subjecting the filtrate to simple distillation.

The residue obtained by the second step, i.e., after separating the unreacted optically active alcohol from the interesterification reaction mixture, may then be hydrolyzed using an alkali, such as sodium hydroxide or potassium hydroxide, or an acid, such as hydrochloric acid or sulfuric acid, and, if desired, fractionated using acetone, methyl ethyl ketone, ethyl acetate, hexane, etc. to obtain an R- or S-form optically active alcohol which has not recovered in the second step with both high chemical purity and high optical purity. It is preferable, however, that the residue of the second step be subsequently used as a starting material of further interesterification for separating the optically active alcohol which has not been separated in the second step. That is, in the third step of the present invention, an optically inactive non-racemic alcohol whose boiling point is different from that of the racemic alcohol used above is added to the residue, and the system is allowed to react under the same reaction conditions as in the first step, i.e., in the presence of a lipase catalyst, in the presence or absence of a solvent, and under a substantially water-free condition. By this second interesterification reaction, the optically active alcohol rich in either one of R- and S-forms which has not been separated in the second step is produced in a free form, which is then isolated in the same manner as in the second step.

The optically inactive non-racemic alcohol to be used is not particularly limited as long its boiling point is different from that of the racemic alcohol used in the first step and it contains no enantiomer. Monohydric alcohols which are used for general purposes in industry would be convenient. Examples of suitable monohydric alcohols are n-butanol, n-pentanol, n-hexanol, cyclohexanol, n-heptanol, n-octanol, n-nonanol, n-decanol, lauryl alcohol, myristyl alcohol, palmityl alcohol, stearyl alcohol, isostearyl alcohol (2-heptylundecanol), oleyl alcohol, n-eicosanol, behenyl alcohol (n-docosanol), n-tricosanol, n-tetracosanol, n-pentacosanol, n-hexacosanol, n-heptacosanol, n-octacosanol, n-nonacosanol, myricyl alcohol, and laccerol. These optically inactive non-racemic alcohols are used either individually or as a mixture of two or more thereof at a residual ester:alcohol molar ratio of 1:≦1, preferably 1:1 to 1:0.5, and the reaction system is allowed to react in the same manner as in the first step. The optically active alcohol rich in either one of R-form and S-form (the enantiomer that has not been reacted in the first step) thus produced in a free form is separated from the reaction mixture.

As the lipase used in the third step, the above-described lipase may be used and, preferably, the above-described heat-resistant lipase may be used. The reaction conditions are the same as those described for the interesterification in the first step.

In a preferred embodiment of the present invention, diester (a) is used in the first step, and for the second reaction an optically inactive non-racemic saturated alcohol having 16 or more carbon atoms is added to the residue to carry out interesterification under the same conditions as used in the first reaction of using heat-resistant lipase (in the presence of heat-resistant lipase as a catalyst, with no solvent, and under a substantially water-free condition) under reduced pressure at a temperature of not lower than 81° C. while simultaneously isolating the optically active alcohol rich in either one of R- and S-forms, which has not been separated from the first reaction mixture, by distillation under reduced pressure.

The optically inactive non-racemic alcohol having 16 or more carbon atoms used above is a saturated alcohol having 16 or more carbon atoms and containing no enantiomer, preferably a straight-chain monohydric alcohol. Examples are palmityl alcohol, 1-heptadecanol, stearyl alcohol, isostearyl alcohol (2-heptylundecanol), oleyl alcohol, n-eicosanol, behenyl alcohol (n-docosanol), n-tricosanol, n-tetracosanol, n-pentacosanol, n-hexacosanol, n-heptacosanol, n-octacosanol, n-nonacosanol, myricyl alcohol, hentriacontanol, and laccerol, with those having 16 to 30 carbon atoms, particularly 18 to 28 carbon atoms, being preferred. Alcohols having less than 16 carbon atoms hardly attain an increased purity in the purification step of the present invention, and those having more than 34 carbon atoms are not easily available on an industrial scale.

These optically inactive non-racemic alcohols are used either individually or as a mixture of two or more thereof at a residual ester:alcohol molar ratio of 1:≦1, preferably 1:1 to 1:0.5. The second interesterification reaction is carried out in the same manner as for the first reaction using heat-resistant lipase, that is, in the presence of heat-resistant lipase, in the absence of a solvent, under a substantially water-free condition, and at a temperature of not lower than 81° C. In this second reaction, it is important to keep the reaction system under reduced pressure (2 to 5 mmHg) so that the produced optically active alcohol rich in either one of R- and S-forms (the enantiomer that has not been separated in the first reaction) may be distilled under reduced pressure and recovered simultaneously with the progress of the interesterification.

The present invention will now be illustrated in greater detail with reference to Examples, but it should be understood that the present invention is not construed as being limited thereto. The chemical purity of the compounds obtained in Examples and Comparative Examples was determined by gas chromatography using GC-14A manufactured by Shimadzu Corp. The optical purity of the compounds was determined by measuring the specific rotation with a polarimeter D1P-370 manufactured by Nippon Bunko K.K. and comparing the measured value with that of a standard preparation.

EXAMPLE 1

In a 300 ml separable flask were put 2 g of Lipase QL of *Alcaligenes sp.* origin (a product of Meito Sangyo Co., Ltd., hereinafter the same applies) and 60 g of (R,S)-1-phenylethanol, and the mixture was subjected to ultrasonication with ultrasonic wave generating equipment SUS-103 manufactured by Shimadzu Corp. at room temperature and at 45 kHz for 1 minute. To the dispersion was added 140 g of dimethyl tetradecadicarboxylate, followed by stirring at 95° C. and 350 rpm for 20 hours to carry out interesterification while evaporating by-produced methanol. The water content of the reaction system was 0.02% by weight as measured by Karl Fischer's method (hereinafter the same applies), and 90% of the lipase particles had a particle size of 10 to 50 µm as measured with a particle size distribution measuring apparatus Multisizer manufactured by Coulter Electronics Inc. (hereinafter the same applies). Gas chromatographic analysis of the reaction mixture revealed that 45 mol % of (R,S)-1-phenylethanol had been converted to 1-(1-phenylethyl),14-methyl tetradecadicarboxylate and 1,14-di(1-phenylethyl) tetradecadicarboxylate.

Lipase was removed by means of Toyo Filter Paper No. 5A, and the filtrate was subjected to simple distillation at 85° C. under reduced pressure of 5 mmHg to give (S)-(−)-1-phenylethanol (yield: 97%; chemical purity: 99.9%; optical purity: 82.3% ee). On the other hand, the residue, i.e., a mixture of 1-(1-phenylethyl),14-methyl tetradecadicarboxylate, 1,14-di(1-phenylethyl) tetradecadicarboxylate, and unreacted dimethyl tetradecadicarboxylate, was alkali-hydrolyzed by refluxing in a 10% sodium hydroxide aqueous solution for 1 hour. To the reaction mixture was added 1000 ml of acetone, followed by cooling to 5° C. The precipitated sodium tetradecadicarboxylate soap was separated by filtration in the same manner as described above, and methanol was evaporated under reduced pressure to give (R)-(+)-1-phenylethanol (yield: 83%; chemical purity: 99.9%; optical purity: 98.3%).

EXAMPLE 2

Interesterification was carried out by using 2 g of Lipase QL, 40 g of (R,S)-1-phenylethanol, and 160 g of diethyl docosadicarboxylate under the same conditions as in Example 1 for a period of 25 hours. The water content of the reaction system was 0.02% by weight, and 96% of the lipase particles had a particle size of 5 to 60 µm. Gas chromatography of the reaction mixture revealed that 49 mol % of (R,S)-1-phenylethanol had been converted to 1-(1-phenylethyl), 20-ethyl docosadicarboxylate and 1,20-di(1-phenylethyl) docosadicarboxylate. The reaction mixture was treated in the same manner as in Example 1 to obtain (S)-(−)-1-phenylethanol (yield: 98%; chemical purity: 99.9%; optical purity: 98.9%). On the other hand, the residue, i.e., a mixture of 1-(1-phenylethyl),20-ethyldocosadicarboxylate, 1,20-di(1-phenylethyl) docosadicarboxylate, and unreacted diethyl docosadicarboxylate was acid-hydrolyzed by refluxing in 10% hydrochloric acid for 1 hour. To the reaction mixture was added 1000 ml of acetone, followed by cooling to 5° C. The precipitated docosadicarboxylic acid was filtered in the same manner as described above, and ethanol was removed by evaporation under reduced pressure to recover (R)-(+)-1-phenylethanol (yield: 87%; chemical purity: 99.9%; optical purity: 98.4% ee).

EXAMPLE 3

In a 300 ml separable flask were put 3 g of Lipase PL of *Alcaligenes sp.* origin (a product of Meito Sangyo Co., Ltd., hereinafter the same applies) and 50 g of (R,S)-1-phenylethanol, and the mixture was subjected to ultrasonication with the same ultrasonic wave generating equipment as used in Example 1 at room temperature and at 20 kHz for 20 minutes. To the dispersion was added 150 g of tripalmitin, followed by stirring at 85° C. and 100 rpm for 30 hours to carry out interesterification. The water content of the reaction system was 0.05% by weight, and 93% of the lipase particles had a particle size of 15 to 40 μm. Gas chromatographic analysis of the reaction mixture revealed that 46 mol % of (R,S)-1-phenylethanol had been converted to 1-phenylethyl palmitate. To the reaction mixture was added 1500 ml of acetone, followed by cooling to 10° C. Lipase, unreacted tripalmitin, dipalmitin, monopalmitin, and palmitic acid were removed by filtration using Toyo Filter Paper No. 5A, and the filtrate was subjected to simple distillation at 95° C. under reduced pressure of 5 mmHg to give (S)-(−)-phenylethanol (yield: 87%; chemical purity: 99.9%; optical purity: 86.3% ee). The residue, i.e., (R)-(+)-1-phenylethanol palmitic acid ester was alkali-hydrolyzed in the same manner as in Example 1 to obtain (R)-(+)-1-phenylethanol (yield: 82%; chemical purity: 99.5%; optical purity: 98.0% ee).

EXAMPLE 4

Interesterification was carried out by using 3 g of Lipase QL, 50 g of (R,S)-1-(2-bromophenyl)ethanol, and 150 g of tribehen under the same conditions as in Example 3 at 105° C. for a period of 20 hours. The water content of the reaction system was 0.01% by weight, and 90% of the lipase particles had a particle size of 30 to 50 μm. Gas chromatography of the reaction mixture revealed that 45 mol % of (R,S)-1-(2-bromophenyl)ethanol had been converted to 1-(2-bromophenyl)ethyl behenate. The reaction mixture was treated in the same manner as in Example 3 and subjected to simple distillation at 110° C. and 5 mmHg to give (S)-(−)-1-(2-bromophenyl)ethanol (yield: 82%; chemical purity: 99.9%; optical purity: 81.5% ee). On the other hand, the residue, i.e., (R)-(+)-1-(2-bromophenyl)ethanol behenic acid ester was acid-hydrolyzed in the same manner as in Example 2 to obtain (R)-(+)-1-(2-bromophenyl)ethanol (yield: 75.6%; chemical purity: 99.8%; optical purity: 99.0% ee).

EXAMPLE 5

Interesterification was carried out by using 3 g of Lipase QL, 50 g of (R,S)-2-octanol, and 150 g of tribehen under the same conditions as in Example 3 at 120° C. for a period of 22 hours. The water content of the reaction system was 0.03% by weight, and 91% of the lipase particles had a particle size of 20 to 40 μm. Gas chromatography of the reaction mixture revealed that 64 mol % of (R,S)-2-octanol had been converted to 2-octyl behenate. The reaction mixture was treated in the same manner as in Example 3 and subjected to simple distillation at 65° C. and 5 mmHg to give (S)-(+)-octanol (yield: 34%; chemical purity: 99.9%; optical purity: 98.2% ee). On the other hand, the residue, i.e., (R)-(−)-2-octyl behenate was alkali-hydrolyzed in the same manner as in Example 1 to obtain (R)-(−)-2-octanol (yield: 85%; chemical purity: 99.6%; optical purity: 62% ee).

EXAMPLE 6

In a 300 ml separable flask were put 1 g of Lipase QL and 40 g of (R,S)-2-decanol, and the mixture was subjected to ultrasonication with the same ultrasonic wave generating equipment as used in Example 1 at room temperature and 90 kHz for 1 minute. To the dispersion was added 60 g of isopropyl stearate, followed by stirring at 95° C. and 250 rpm for 20 hours to carry out interesterification while evaporating by-produced isopropyl alcohol under reduced pressure. The water content of the reaction system was 0.02% by weight, and 96% of the lipase particles had a particle size of 10 to 40 μm. Gas chromatographic analysis of the reaction mixture revealed that 58 mol % of (R,S)-2-decanol had been converted to 2-decyl stearate. Lipase was removed by filtration in the same manner as in Example 1, and the filtrate was subjected to simple distillation at 70° C. under reduced pressure of 5 mmHg to give (S)-(+)-2-decanol (yield: 73.5%; chemical purity: 99.9%; optical purity: 98.5% ee). The residue, i.e., a mixture of (R)-(−)-2-decanol stearic acid ester and unreacted isopropyl stearate was acid-hydrolyzed in the same manner as in Example 2, and 1000 ml of acetone was added to the reaction mixture, followed by cooling to 5° C. The precipitated stearic acid was removed by filtration, and methanol was evaporated from the filtrate under reduced pressure to give (R)-(−)-2-decanol (yield: 72%; chemical purity: 99.6%; optical purity: 84% ee).

EXAMPLE 7

Interesterification was carried out by using 1 g of Lipase QL, 40 g of (R,S)-1-phenylethanol, and 60 g of ethyl behenate under the same conditions as in Example 6 at 95° C. for a period of 20 hours. The water content of the reaction system was 0.03% by weight, and 95% of the lipase particles had a particle size of 20 to 40 μm. Gas chromatography of the reaction mixture revealed that 47 mol % of (R,S)-1-phenylethanol had been converted to 1-phenylethyl behenate. The reaction mixture was treated in the same manner as in Example 6 and subjected to simple distillation at 85° C. and 5 mmHg to give (S)-(−)-1-phenylethanol (yield: 97%; chemical purity: 99.9%; optical purity: 88.9% ee). On the other hand, the residue, i.e., a mixture of (R)-(+)-1-phenylethyl behenate and unreacted ethyl behenate was alkali-hydrolyzed in the same manner as in Example 1, and 1000 ml of acetone was added to the reaction mixture, followed by cooling to 5° C. The precipitated behenic acid was removed by filtration to obtain (R)-(+)-1-phenylethanol (yield: 88%; chemical purity: 99.9%; optical purity: 98.5% ee).

COMPARATIVE EXAMPLE 1

Interesterification was carried out in the same manner as in Example 4, except for replacing tribehen with 150 g of tributyrin, at 40° C. for 25 hours. The water content of the reaction system was 0.05% by weight, and 93% of the lipase particles had a particle size of 20 to 40 μm. The reaction mixture was fractionated into fractions of alcohol, monoester, fatty acid, monoglyceride, diglyceride, and triglyceride by thin layer chromatography, and the reaction rate was determined by gas chromatography. As a result, it was found that 37 mol % of (R,S)-1-(2-bromophenyl)ethanol had been converted to 1-(2-bromophenyl)ethyl butyrate. The reaction mixture was treated in the same manner as in Example 4, and the filtrate was subjected to simple distillation at 110° C. and 5 mmHg aiming at recovery of (S)-(−)-1-(2-bromophenyl)ethanol. However, it was impossible to isolate only the desired compound due to contamination of other components.

COMPARATIVE EXAMPLE 2

Interesterification was carried out in the same manner as in Example 7, except for replacing ethyl behenate with 60 g of ethyl laurate at 40° C. for 25 hours. The water content of the reaction system was 0.03% by weight, and 94% of the lipase particles had a particle size of 10 to 50 µm. Gas chromatography of the reaction mixture revealed conversion of 46 mol % of (R,S)-1-phenylethanol to 1-phenylethyl laurate. The reaction mixture was treated in the same manner as in Example 7, and the filtrate was subjected to simple distillation at 85° C. and 5 mmHg to recover (S)-(−)-1-phenylethanol with a chemical purity of 32%. The product was purified by liquid chromatography to recover (S)-(−)-1-phenylethanol in a yield of 5%. The optical purity was 89% ee.

EXAMPLE 8

In a 1000 ml separable flask were put 10 g of Lipase OF of *Candida cylindoracea* origin (a product of Meito Sangyo Co., Ltd.), 80 g of (R,S)-1-phenylethanol, 140 g of dimethyl octadecadicarboxylate, and 420 ml of hexane, and the mixture was subjected to ultrasonication with the same ultrasonic wave generating equipment as used in Example 1 at room temperature and at 45 kHz for 1 minute. Thereafter, the mixture was stirred at 50° C. at 350 rpm for 72 hours to carry out interesterification. The water content of the reaction system was 0.05% by weight, and 95% or more of the lipase particles had a particle size of 20 to 50 µm. Gas chromatographic analysis of the reaction mixture revealed conversion of 49 mol % of (R,S)-1-phenylethanol to octadecadicarboxylic acid esters.

Lipase was removed by filtration using a membrane filter (0.5 µm) (produced by Advantec Co., hereinafter the same applies), and hexane was evaporated under reduced pressure. The residue was subjected to simple distillation at 90° C. under reduced pressure of 3 mmHg to recover unreacted (S)-(−)-phenylethanol (yield: 98%; chemical purity: 100%; optical purity: 98% ee).

To the distillation residue were added 270 g of n-tetradecanol, 450 ml of hexane, and 10 g of Lipase OF. After regulating the particle size of the lipase by ultrasonication in the same manner as above, the mixture was stirred at 50° C. and 350 rpm for 72 hours to carry out interesterification. Hexane was evaporated under reduced pressure from the reaction mixture, and the residue was subjected to simple distillation at 90° C. and 3 mmHg to give highly pure (R)-(+)-1-phenylethanol in a free form (yield: 87%; chemical purity: 100%; optical purity: 100% ee).

COMPARATIVE EXAMPLE 3

Interesterification was carried out in the same manner as in Example 8, except for replacing dimethyl octadecadicarboxylate with 150 g of dimethyl sebacate at 50° C. for 72 hours. The water content of the reaction system was 0.07% by weight, and 87% of the lipase particles had a particle size of 25 to 60 µm. After completion of the reaction, gas chromatography of the reaction mixture revealed conversion of 32 mol % of (R,S)-1-phenylethanol to a sebacic acid ester. The reaction mixture was treated in the same manner as in Example 8 to remove lipase and hexane, and the residue was subjected to simple distillation at 90° C. and 3 mmHg. However, the distillate contained not only unreacted (S)-(−)-1-phenylethanol but other components such as esters, resulting in a failure of recover of the S-form.

To the distillation residue were added 220 g of nonanol and 10 g of the same lipase as used in Example 8, and interesterification was carried out at 50° C. for 72 hours. The reaction mixture was treated and subjected to simple distillation at 90° C. and 3 mmHg, but (R)-(+)-1-phenylethanol could not be isolated due to contamination of other components, such as unreacted nonanol and esters.

EXAMPLE 9

In a 300 ml separable flask were put 4.5 g of Lipase QL, 90 g of (R,S)-2-octanol, and 134 g of dimethyl tetradecadicarboxylate, and the mixture was subjected to ultrasonication with the same ultrasonic wave generating equipment as used in Example 1 at room temperature and 45 kHz for 1 minute. The mixture was stirred at 105° C. at 350 rpm for 25 hours to carry out interesterification while evaporating by-produced methanol. The water content of the reaction system was 0.02% by weight, and 90% or more of the lipase particles had a particle size of 20 to 50 µm. After completion of the reaction, gas chromatographic analysis of the reaction mixture revealed that 48 mol % of (R,S)-2-octanol had been converted to its tetradecadicarboxylic acid esters.

Lipase was removed by filtration using a membrane filter (0.5 µm), and the filtrate was subjected to simple distillation at 95° C. under reduced pressure of 3 mmHg to give unreacted (S)-(+)-2-octanol (yield: 95%; chemical purity: 100.2%; optical purity: 95% ee).

To the distillation residue were added 180 g of oleyl alcohol and 8 g of Lipase QL. After regulating the particle size of the lipase by ultrasonication in the same manner as described above, the mixture was stirred at 105° C. and 350 rpm for 48 hours to carry out interesterification. The resulting reaction mixture was subjected to simple distillation at 95° C. and 3 mmHg to give highly pure (R)-(−)-2-octanol in a free form (yield: 92%; chemical purity: 100.9%; optical purity: 100% ee).

COMPARATIVE EXAMPLE 4

Interesterification was carried out in the same manner as in Example 9, except for replacing dimethyl tetradecadicarboxylate with 140 g of dimethyl decamethylenedicarboxylate at 80° C. for 25 hours. The water content of the reaction system was 0.04% by weight, and 95% of the lipase particles had a particle size of 20 to 60 µm. Gas chromatography of the reaction mixture revealed that 58 mol % of (R,S)-2-octanol had been converted to its decamethylenedicarboxylic acid ester. The reaction mixture was treated in the same manner as in Example 9 to remove lipase, and the filtrate was subjected to simple distillation at 95° C. and 3 mmHg. However, it was impossible to isolate (S)-(−)-2-octanol with high purity due to co-distillation of other components.

To the distillation residue were added 300 g of n-decanol and 10 g of the same lipase as used in Example 9, and interesterification was carried out at 80° C. for 48 hours in the same manner. The reaction mixture was treated and subjected to simple distillation at 95° C. and 3 mmHg only to recover (R)-(+)-2-octanol having a chemical purity of only 61% and an optical purity of only 78% ee.

EXAMPLE 10

Interesterification was carried out by using 5 g of Lipase P of *Pseudomonas fluorescens* origin (a product of Amano Pharmaceutical Co., Ltd.), 10 g of (R,S)-1-2-(bromophenyl)ethanol, 30 g of tribehen and 450 ml of cyclohexane at 50° C. for 72 hours in the same manner as in Example 8. The water content of the reaction system was 0.01% by weight, and 90% of the lipase particles had a particle size of 30 to 50 µm. Gas chromatography of the reaction mixture revealed that 48 mol % of (R,S)-1-(2-bromophenyl)ethanol had been converted to 1-(2-bromophenyl)ethyl behenate. The reaction mixture was treated in the same manner as in Example 8, and the residue was subjected to simple distillation at 110° C. and 5 mmHg to recover unreacted (S)-(−)-1-(2-bromophenyl)ethanol (yield: 82%; chemical purity: 99.9%; optical purity: 98% ee).

To the distillation residue were added 30 g of lauryl alcohol, 350 ml of cyclohexane, and 3 g of Lipase P. After regulating the particle size of the enzyme by ultrasonication in the same manner as described above, interesterification was carried out at 50° C. for 68 hours. The reaction mixture was subjected to simple distillation at 110° C. and 5 mmHg to recover highly pure (R)-(+)-1-(2-bromophenyl)ethanol in a free form (yield: 75.6%; chemical purity: 99.8%; optical purity: 99% ee or higher).

EXAMPLE 11

In a 300 ml separable flask were put 1 g of Lipase PL, and 40 g of (R,S)-2-decanol, and the mixture was subjected to ultrasonication with the same ultrasonic wave generating equipment as used in Example 1 at room temperature and 90 kHz for 1 minute. To the mixture was added 60 g of isopropyl stearate, followed by stirring at 85° C. and 250 rpm for 30 hours to carry out interesterification. The water content of the reaction system was 0.02% by weight, and 96% of the lipase particles had a particle size of 10 to 40 μm. Gas chromatographic analysis of the reaction mixture revealed that 57 mol % of (R,S)-2-decanol had been converted to 2-decyl stearate. Lipase was removed by filtration in the same manner as in Example 8, and the filtrate was subjected to simple distillation at 70° C. and 5 mmHg to recover unreacted (S)-(+)-2-decanol (yield: 73.5%; chemical purity: 99.9%; optical purity: 93% ee).

To the distillation residue, i.e., a mixture of (R)-(−)-2-decanol stearic acid ester and unreacted isopropyl stearate, were added 90 g of stearyl alcohol and 3 g Lipase PL. After regulating the particle size of the enzyme by ultrasonication in the same manner as described above, interesterification was carried out at 85° C. for 48 hours. The reaction mixture was subjected to simple distillation at 90° C. and 3 mmHg to recover highly pure free (R)-(−)-2-decanol (yield: 72%; chemical purity: 99.6%; optical purity: 84% ee).

EXAMPLE 12

In a 300 ml separable flask were put 10 g of Lipase PL, 80 g of (R,S)-1-phenylethanol, and 140 g of dimethyl octadecadicarboxylate, and the mixture was subjected to ultrasonication with the same ultrasonic wave generating equipment as used in Example 1 at room temperature and 45 kHz for 1 minute. The mixture was stirred at 90° C. and 350 rpm for 30 hours to carry out interesterification. The water content of the reaction system was 0.05% by weight, and 95% or more of the lipase particles had a particle size of 20 to 50 μm. Gas chromatographic analysis of the reaction mixture revealed that 49 mol % of (R,S)-1-phenylethanol had been converted to octadecadicarboxylates.

Lipase was removed by filtration using a membrane filter (0.5 μm), and the filtrate was subjected to simple distillation at 90° C. under reduced pressure of 3 mmHg to give unreacted (S)-(−)-1-phenylethanol (yield: 98%; chemical purity: 100%; optical purity: 99% ee).

To the distillation residue were added 270 g of stearyl alcohol and 10 g of Lipase PL. The mixture was subjected to ultrasonication in the same manner as described above to regulate the particle size of the lipase in such a manner that 95% or more of the particles had a particle size of 20 to 50 μm. The water content of the reaction system was 0.04% by weight. The mixture was stirred at 90° C. and 350 rpm under reduced pressure of 3 mmHg for 12 hours to carry out interesterification while recovering the distillate to obtain highly pure (R)-(+)-1-phenylethanol (yield: 96%; chemical purity: 100%; optical purity: 100% ee).

COMPARATIVE EXAMPLE 5

The second interesterification reaction of Example 12 was carried out under atmospheric pressure at 90° C. for 24 hours. The resulting reaction mixture was subjected to simple distillation at 90° C. and 3 mmHg to obtain (R)-(+)-1-phenylethanol (chemical purity: 100%; optical purity: 100% ee) in a yield of 83%.

COMPARATIVE EXAMPLE 6

Interesterification was carried out in the same manner as in Example 12, except for replacing dimethyl octadecadicarboxylate with 150 g of dimethyl sebacate at 90° C. for 30 hours. The water content of the reaction system was 0.07% by weight, and 87% of the lipase particles had a particle size of 25 to 60 μm. After completion of the reaction, gas chromatography of the reaction mixture revealed that 42 mol % of (R,S)-1-phenylethanol had been converted to its sebacic acid ester. The reaction mixture was treated in the same manner as in Example 12 to remove lipase, and the filtrate was subjected to simple distillation at 90° C. and 3 mmHg. However, it was impossible to isolate (S)-(−)-1-phenylethanol due to co-distillation of other components, such as esters.

To the distillation residue were added 220 g of nonanol and 10 g of the same lipase as used in Example 12, and interesterification was carried out at 90° C. under reduced pressure of 3 mmHg while recovering the distillate. However, it was impossible to isolate (R)-(+)-1-phenylethanol due to co-distillation of other components, such as unreacted nonanol and esters.

EXAMPLE 13

In a 300 ml separable flask were put 4.5 g of Lipase QL, 90 g of (R,S)-2-octanol, and 134 g of dimethyl tetradecadicarboxylate, and the mixture was subjected to ultrasonication with the same ultrasonic wave generating equipment as used in Example 1 at room temperature and 45 kHz for 1 minute. The mixture was stirred at 105° C. at 350 rpm for 25 hours to carry out interesterification while evaporating by-produced methanol. The water content of the reaction system was 0.02% by weight, and 90% or more of the lipase particles had a particle size of 20 to 50 μm. After completion of the reaction, gas chromatographic analysis of the reaction mixture revealed that 48 mol % of (R,S)-2-octanol had been converted to its tetradecadicarboxylic acid esters. The reaction mixture was subjected to simple distillation at 95° C. under reduced pressure of 3 mmHg to give unreacted (S)-(+)-2-octanol (yield: 95%; chemical purity: 100.2%; optical purity: 95% ee).

To the distillation residue was added 140 g of palmityl alcohol, and the mixture was stirred at 95° C. and 350 rpm under reduced pressure of 3 mmHg for 20 hours to carry out interesterification while recovering the distillate to obtain highly pure (R)-(−)-2-octanol (yield: 96%; chemical purity: 100.9%; optical purity: 100% ee).

COMPARATIVE EXAMPLE 7

The second interesterification reaction of Example 13 was carried out under atmospheric pressure at 95° C. for 24 hours. The resulting reaction mixture was subjected to simple distillation at 95° C. under reduced pressure of 3 mmHg to obtain (R)-(−)-2-octanol (chemical purity: 100.3%; optical purity: 100% ee) in a yield of 87%.

COMPARATIVE EXAMPLE 8

Interesterification was carried out in the same manner as in Example 13, except for replacing dimethyl tetradecadicarboxylate with 140 g of dimethyl decamethylenedicarboxylate at 80° C. for 25 hours. The water content of the reaction system was 0.04% by weight, and 95% of the lipase particles had a particle size of 20 to 60 µm. Gas chromatography of the reaction mixture revealed that 58 mol % of (R,S)-2-octanol had been converted to its decamethylenedicarboxylic acid esters. The reaction mixture was treated in the same manner as in Example 13 to remove lipase, and the filtrate was subjected to simple distillation at 95° C. and 3 mmHg. It was impossible to isolate (S)-(−)-2-octanol with high purity due to co-distillation of other components.

To the distillation residue were added 300 g of n-decanol and 10 g of the same lipase as used in Example 13, and interesterification was carried out at 95° C. under reduced pressure of 3 mmHg while recovering (R)-(+)-2-octanol as a distillate. However, the product had a chemical purity of only 78% and an optical purity of only 61% ee.

EXAMPLE 14

Interesterification was carried out by using 3 g of Lipase QL, 50 g of (R,S)-1-(2-bromophenyl)ethanol, and 150 g of tribehen at 120° C. for 20 hours in the same manner as in Example 12. The water content of the reaction system was 0.01% by weight, and 90% of the lipase particles had a particle size of 30 to 50 µm. Gas chromatography of the reaction mixture revealed that 44 mol % of (R,S)-1-(2-bromophenyl)ethanol had been converted to 1-(2-bromophenyl)ethyl behenate. The reaction mixture was treated in the same manner as in Example 12, and the filtrate was subjected to simple distillation at 110° C. and 5 mmHg to recover unreacted (S)-(−)-1-(2-bromophenyl)ethanol (yield: 88%; chemical purity: 99.9%; optical purity: 99% ee or higher).

To the distillation residue were added 180 g of behenyl alcohol and 5 g of Lipase QL. After regulating the particle size of the enzyme by ultrasonication in the same manner as described above, interesterification was carried out at 110° C. under reduced pressure of 5 mmHg for 24 hours while recovering the distillate to collect (R)-(+)-1-(2-bromophenyl)ethanol with high purity (yield: 83%; chemical purity: 99.8%; optical purity: 99% ee or higher).

EXAMPLE 15

In a 300 ml separable flask were put 1 g of Lipase PL and 40 g of (R,S)-2-decanol, and the mixture was subjected to ultrasonication with the same ultrasonic wave generating equipment as used in Example 1 at room temperature and 90 kHz for 1 minute. To the mixture was added 60 g of isopropyl stearate, followed by stirring at 85° C. at 250 rpm for 30 hours to carry out interesterification. The water content of the reaction system was 0.02% by weight, and 96% of the lipase particles had a particle size of 10 to 40 µm. Gas chromatographic analysis of the reaction mixture revealed that 57 mol % of (R,S)-2-decanol had been converted to 2-decyl stearate. Lipase was separated by filtration in the same manner as in Example 12, and the filtrate was subjected to simple distillation at 70° C. and 5 mmHg to give unreacted (S)-(+)-2-decanol (yield: 73.5%; chemical purity: 99.9%; optical purity: 95% ee).

To the distillation residue, i.e., a mixture of (R)-(−)-2-decanol stearic acid ester and unreacted isopropyl stearate, were added 200 g of palmityl alcohol and 3 g of Lipase PL. After the particle size of the enzyme was regulated by ultrasonication in the same manner as described above, the mixture was stirred at 90° C. and 250 rpm under reduced pressure of 2 mmHg for 24 hours to carry out interesterification while recovering the distillate to obtain free (R)-(−)-2-decanol with high purity (yield: 72%; chemical purity: 99.6%; optical purity: 95% ee).

EXAMPLE 16

In a 300 ml separable flask were put 4.5 g of Lipase QL, 90 g of (R,S)-1-phenyl-1-propanol, and 135 g of dimethyl octadecadicarboxylate. After the same ultrasonication as in Example 12, the mixture was subjected to interesterification by stirring at 85° C. and 300 rpm for 24 hours. The water content of the reaction system was 0.04% by weight, and 90% or more of the lipase particles had a particle size of 20 to 50 µm. Gas chromatographic analysis of the reaction mixture revealed that 49 mol % of (R,S)-1-phenyl-1-propanol had been converted to its octadecadicarboxylic acid esters. Lipase was separated by filtration using a membrane filter (0.5 µm), and the filtrate was subjected to simple distillation at 95° C. and 3 mmHg to recover unreacted (S)-(−)-1-phenyl-1-propanol (yield: 90%; chemical purity: 100%; optical purity: 99% ee or higher).

To the distillation residue were added 290 g of stearyl alcohol and 12 g of Lipase QL. After the particle size of the enzyme was regulated by ultrasonication in the same manner as described above, the mixture was stirred at 95° C. and 350 rpm and 3 mmHg for 28 hours to carry out interesterification while recovering the distillate to obtain (R)-(+)-1-phenyl-1-propanol (yield: 87%; chemical purity: 100%; optical purity: 100% ee).

EXAMPLE 17

In a 500 ml separable flask were put 7 g of Lipase QL, 157 g of (R,S)-1-(p-chlorophenyl)ethanol, and 185 g of dimethyl octadecadicarboxylate. After the same ultrasonication as in Example 12, the mixture was subjected to interesterification by stirring at 90° C. and 300 rpm for 24 hours. The water content of the reaction system was 0.05% by weight, and 95% or more of the lipase particles had a particle size of 20 to 50 µm. Gas chromatographic analysis of the reaction mixture revealed conversion of 48 mol % of (R,S)-1-(p-chlorophenyl)ethanol to its octadecadicarboxylic acid esters. The reaction mixture was subjected to simple distillation at 95° C. and 3 mmHg to recover unreacted (S)-(−)-1-(p-chlorophenyl)ethanol (yield: 92%; chemical purity: 97%; optical purity: 94% ee).

To the distillation residue were added 195 g of stearyl alcohol and 4 g of Lipase QL. After the particle size of the enzyme was regulated by ultrasonication in the same manner as described above, the mixture was stirred at 95° C. and 350 rpm under reduced pressure of 3 mmHg for 30 hours to carry out interesterification while recovering the distillate to collect (R)-(+)-1-(p-chlorophenyl)ethanol (yield: 82%; chemical purity: 100%; optical purity: 100% ee).

According to the present invention, each of R- and S-form optically active alcohols can easily be recovered with high purity in high yield. That is, in the first interesterification reaction either one of the enantiomers remains unreacted, while the other is selectively converted to an ester having a high melting point and a high boiling point. Therefore, the difference in the melting point or boiling point can be taken advantage of for recovering the unreacted optically active alcohol with high chemical and optical purity in good yield by a convenient and inexpensive purification means, such as simple distillation or solvent fractionation. In the subsequent second reaction, interesterification is effected between the residue of the first reaction and an optically inactive non-racemic alcohol thereby to release either R- or S-form optically active alcohol which has not been recovered in the previous step. The thus released optically active alcohol can be isolated through a simple means as used in the previous step to achieve increased chemical and optical purity. Further, where heat-resistant lipase is used in the interesterification reaction, there is no need to use a solvent for the starting material, an ester having a high melting point can be used in the process, and the reaction can be performed at a high temperature not heretofore feasible, making it possible to complete the reaction in an extremely reduced time. Furthermore, where the second interesterification reaction is carried out under reduced pressure, the enantiomer that has not been separated in the first reaction can easily be isolated at high chemical and optical purity in high yield simultaneously with the reaction progress.

While the invention has been described in detail and with reference to specific examples thereof, it will be apparent to one skilled in the art that various changes and modifications can be made therein without departing from the spirit and scope thereof.

What is claimed is:

1. A process for producing an optically active alcohol comprising the steps of:

carrying out interesterification between a racemic alcohol and an ester selected from the group consisting of (a) a diester between a lower monohydric alcohol and a saturated dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms in the presence of heat-resistant lipase and in the absence of a solvent under a substantially water-free condition at a temperature of not lower than 81° C. and separating an optically active alcohol rich in either one of R- and S-forms from the reaction mixture.

2. A process for producing an optically active alcohol comprising the steps of:

carrying out interesterification between a racemic alcohol and an ester selected from the group consisting of (a) a diester between a lower monohydric alcohol and a saturate dicarboxylic acid having 14 or more carbon atoms, (b) a triglyceride of a saturated fatty acid having 16 or more carbon atoms, and (c) a monoester between a lower monohydric alcohol and a saturated fatty acid having 18 or more carbon atoms in the presence of lipase and in the presence or absence of a solvent under a substantially water-free condition, separating the resulting reaction mixture into an optically active alcohol rich in either one of R- and S-forms and the residue, adding an optically inactive non-racemic alcohol having a different boiling point from that of said racemic alcohol to said residue to carry out interesterification in the presence of lipase and in the presence or absence of a solvent under a substantially water-free condition, and separating an optically active alcohol rich in either one of R- and S-forms which has not been separated in the second step.

3. A process for producing an optically active alcohol comprising the steps of:

carrying out interesterification between a racemic alcohol and a diester between a lower monohydric alcohol and a saturated dicarboxylic acid having 14 or more carbon atoms in the presence of heat-resistant lipase and in the absence of a solvent under a substantially water-free condition at a temperature not lower than 81° C., separating the resulting reaction mixture into an optically active alcohol rich in either one of R- and S-forms and the residue, and adding an optically inactive non-racemic saturated alcohol having 16 or more carbon atoms to said residue to carry out interesterification in the presence of heat-resistant lipase and in the absence of a solvent under a substantially water-free condition at a temperature of not lower than 81° C. and under reduced pressure while separating an optically active alcohol rich in either one of R- and S-forms which has not been separated in the second step by reduced pressure distillation.

4. A process for producing an optically active alcohol according to claim 1, 2 or 3, wherein said saturated dicarboxylic acid and said saturated fatty acid have a straight chain.

5. A process for producing an optically active alcohol according to claim 1, 2 or 3, wherein said lipase or heat-resistant lipase has a powdered form and at least 90% (as an absolute number) of said lipase has a particle size of from 1 to 100 μm.

6. A process for producing an optically active alcohol according to claim 1, 2 or 3, wherein said racemic alcohol is a 2-alkanol.

7. A process for producing an optically active alcohol according to claim 1, 2 or 3, wherein said racemic alcohol is a compound represented by formula (I):

wherein A and B are different from each other; A represents a phenyl group or a substituent represented by formula (II):

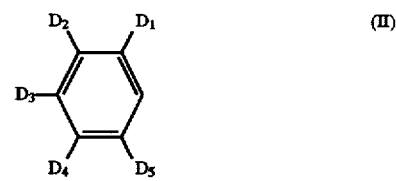

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms;

and B represents an alkyl group having 1 to 3 carbon atoms, a trifluoromethyl group or a cyano group.

8. The process for producing an optically active alcohol according to claim 2, wherein the lipase is a heat-resistant lipase and the interesterification is carried out at a temperature of not lower than 81° C.

9. A process for producing an optically active alcohol according to claim 1, 3 or 8, wherein said heat-resistant lipase is a heat-resistant lipase produced by a microorganism belonging to the genus Alcaligenes.

10. A process for producing an optically active alcohol according to claim 1, 3 or 8, wherein the interesterification using heat-resistant lipase is carried out at the temperature of from 101° to 120° C.

* * * * *